United States Patent [19]

Takanashi et al.

[11] Patent Number: 5,575,285
[45] Date of Patent: Nov. 19, 1996

[54] APPARATUS FOR MEASURING OXYGEN SATURATION

[75] Inventors: Satohiko Takanashi, Chofu; Tetsuya Yamamoto, Tsukuba; Tsuyoshi Watanabe; Muneharu Ishikawa, both of Chofu, all of Japan

[73] Assignee: Kowa Company Limited, Japan

[21] Appl. No.: 355,516

[22] Filed: Dec. 14, 1994

[30] Foreign Application Priority Data

Dec. 21, 1993 [JP] Japan ................... 5-320721

[51] Int. Cl.$^6$ ...................................... A61B 5/00
[52] U.S. Cl. ............................. 128/633; 356/41
[58] Field of Search ..................... 128/633, 664; 356/41

[56] References Cited

U.S. PATENT DOCUMENTS

| | | |
|---|---|---|
| 4,759,369 | 7/1988 | Taylor ........................ 128/664 |
| 4,807,631 | 2/1989 | Hersh et al. ................. 356/41 |
| 5,078,136 | 1/1992 | Stone et al. ................. 128/633 |
| 5,094,239 | 3/1992 | Jaeb et al. ................... 128/633 |
| 5,111,817 | 5/1992 | Clark et al. ................. 128/633 |
| 5,277,181 | 1/1994 | Mendelson et al. ........ 356/41 |
| 5,285,782 | 2/1994 | Prosser ....................... 128/664 |
| 5,285,783 | 2/1994 | Secker ........................ 128/633 |
| 5,308,919 | 5/1994 | Minnich ..................... 128/633 |
| 5,353,791 | 10/1994 | Tamura et al. .............. 128/633 |
| 5,372,136 | 12/1994 | Stever et al. ................ 128/633 |
| 5,386,827 | 2/1995 | Chance et al. .............. 128/633 |

*Primary Examiner*—Angela D. Sykes
*Assistant Examiner*—Eric F. Winakur
*Attorney, Agent, or Firm*—Adams & Wilks

[57] ABSTRACT

An apparatus for non-invasively measuring the oxygen saturation in the blood of a subject comprises light sources for irradiating a sample of blood in tissue with at least a first light beam and a second light beam having different wavelengths. A switching device drives the light sources and sequentially switches the irradiation of the sample of blood between the first and second laser beams. A photoelectric detector detects light transmitted through or reflected from the sample of blood and provides an electrical output signal indicative of the intensity of the detected light. A converter converts the electrical output signal of the photoelectric detecting device to a power spectrum, and a processor processes the power spectrum and calculates the oxygen saturation of the sample of blood. The blood oxygen saturation in the blood can be measured with high accuracy based on the detection of the light intensity transmitted through or reflected from the blood, regardless of the presence or absence of a pulsed blood flow. Additionally, by irradiating the subject by switching between laser beams of two wavelengths, the subject receives less irradiation than when two lasers are used at the same time. Thus even if the amount of irradiation at each wavelength is slightly increased, the accuracy measurement can be improved without adversely affecting the subject.

16 Claims, 4 Drawing Sheets

APPARATUS FOR MEASURING OXYGEN SATURATION

BACKGROUND OF THE INVENTION

1. Field of the Invention

The present invention relates to an apparatus for non-invasively measuring the degree of oxygen saturation in blood, and more particularly to an apparatus for non-invasively measuring the oxygen saturation by utilizing the optical absorption and scattered light characteristics of hemoglobin contained in red blood corpuscles.

2. Description of the Prior Art

There is a conventional apparatus for non-invasive measurement of oxygen saturation known as a pulse oximeter. A pulse oximeter works by measuring changes in transmittance accompanying the pulsing of arterial blood, and calculating the oxygen saturation of red blood corpuscle hemoglobin. Focussing also on red blood corpuscles in blood vessels, JP-A-HEI-4-15046 discloses a speckle oximetry method of measuring blood oxygen saturation.

As pulse oximetry measures changes in transmittance accompanying arterial blood pulses, it may be unable to detect the pulse when peripheral blood vessels are contracted, such as when a subject is in shock, for example. In such cases measurement can be difficult or impossible. Measurement also becomes difficult when the pulse is very weak owing to heavy hemorrhaging. Moreover, it is very difficult to measure the degree of oxygen saturation in venous blood.

It was to resolve such problems that the speckle oximetry method was prepared in JP-A-HEI-4-15046. In the speckle oximetry method a plurality of laser beams with different wavelengths are focussed simultaneously on a living subject, the light scattered therefrom is separated into the different wavelengths, and the oxygen saturation of the blood is measured from the intensity fluctuations of each wavelength.

However, there is a limit to the laser beam irradiation intensity that can be used on a living subject, and irradiation by a plurality of high power laser beams is not possible. Moreover, it is desirable to decrease the intensity of the laser beam that is used to avoid low-temperature burns to the living tissue. A low intensity is also desirable from the standpoint of ease of handling. When using a plurality of laser beams simultaneously, even if the intensity of individual beams is low, the effect that the total amount of irradiation involved can have on living tissues becomes a problem. If the output of each laser is decreased further in an attempt to solve the problem, the result is a lower signal-to-noise (S/N) ratio, lowering the accuracy of measurements.

An object of the present invention is to provide an apparatus that irradiates a living subject with coherent light, such as a laser beam, to non-invasively measure the oxygen saturation of hemoglobin in red blood corpuscles, and can readily and accurately measure oxygen saturation whether in arterial blood with a very weak pulse or in a blood flow with no pulse such as venous blood, and which moreover can reduce the amount of laser beam irradiation to which the living body is subjected.

SUMMARY OF THE INVENTION

The above object is achieved in accordance with this invention by an apparatus for measuring oxygen saturation non-invasively by irradiating a living subject with coherent light, such as a laser beam, measuring the intensity of light scattered or transmitted which contains frequency components corresponding to blood flow, and using the measurement result to measure the oxygen saturation of hemoglobin in red blood corpuscles in the blood. The apparatus comprises a plurality of light sources each of which produces coherent light having a wavelength different from each other, switching means for sequentially switching and driving the plurality of light sources, photoelectric conversion means for receiving light scattered or transmitted from the subject irradiated by the coherent light from the light sources sequentially switched on and driven by the switching means, and converting the intensity of such scattered or reflected light to an electrical signal, and processing means for processing the electrical signal produced by the photoelectric conversion means and calculating the oxygen saturation of the hemoglobin.

In accordance with this arrangement, regardless of whether a blood flow is arterial and therefore has a pulse, or is venous and therefore does not have a pulse, light that is scattered or absorbed by blood corpuscles can be detected and the transmitted light intensity or scattered light intensity measured, enabling the intensity of light containing frequency components corresponding to the blood flow to be obtained. By using a plurality of coherent beams of light having different wavelengths, the intensity of light having a frequency component corresponding to the blood flow can be obtained for each wavelength, and these intensities can be used as a basis for calculating the oxygen saturation of hemoglobin in the red blood corpuscles. Furthermore, this arrangement in which coherent beams of light of different wavelength are sequentially switched makes possible a considerable reduction in the total irradiation amount compared to simultaneous irradiation by plural laser beams.

Further features of the invention, its nature and various advantages will be more apparent from the accompanying drawings and following detailed description of the invention.

DESCRIPTION OF THE PREFERRED EMBODIMENT

Figure 1:
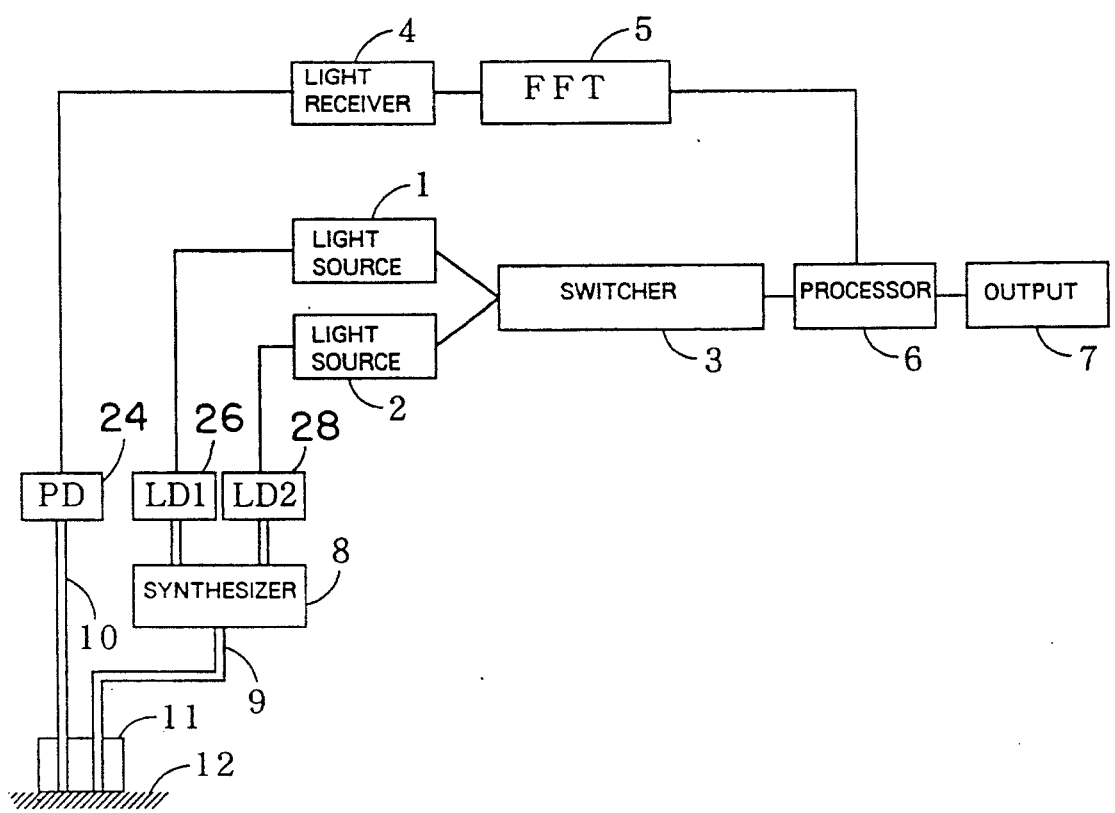
FIG. 1 is a block diagram showing the arrangement of a first embodiment of the oxygen saturation measurement apparatus of the invention.

FIG. 1 shows the arrangement of a first embodiment of an apparatus for measuring oxygen saturation by non-invasive means, according to this invention. The apparatus is provided with two laser light beam sources which produce laser beams with different wavelengths for irradiating a subject, and obtains the degree of oxygen saturation by measuring scattered light from the subject.

The apparatus of FIG. 1 consists of light sources 1 and 2, a light source switcher 3, a light receiver 4, an FFT section 5, a processor 6 and an output section 7. The light sources 1 and 2 emit beams of laser light having mutually different wavelengths. The light sources 1 and 2 are operated sequentially by being switched under the control of the processor 6. The light sources 1 and 2 are constituted by laser diode 26 (LD1) and 28 (LD2), and the light thus produced passes along different optical systems to a synthesizer 8 where the two beams are combined and guided into a projection optical fiber 9 to irradiate a living subject 12.

The wavelengths of the laser beams emitted by the light sources 1 and 2 are set based on a consideration of the spectral characteristics of oxygen hemoglobin and reduced hemoglobin. For example, light source 1 has a wavelength in the region of 680 nm, the large difference between the light absorption of oxygen hemoglobin and reduced hemoglobin, while light source 2 has a wavelength in the region of 805 nm, the wavelength of the isosbestic point of oxygen hemoglobin and reduced hemoglobin. The selection of these wavelengths ensures the precise measurement of the oxygen saturation.

While this arrangement uses laser beams with just two wavelengths, three wavelengths can be used to eliminate the light absorption effect of living body tissues. With respect to the third laser beam, oxygen saturation can be measured with better accuracy if a frequency is chosen that is on the longer wavelength side of the frequency region where spectral characteristics of oxygen hemoglobin and reduced hemoglobin undergo a reversal, that is, a wavelength longer than 805 nm. However, at around 900 nm there is a water absorption region in which oxygen saturation cannot be measured with good efficiency. Within the frequency region where spectral characteristics of oxygen hemoglobin and reduced hemoglobin undergo reversal, a preferable wavelength is around 830 nm, where there is a relatively large difference in absorbance.

The light sources 1 and 2 emitting the laser beam are switched by the light source switcher 3 under the signal control of the processor 6. The light source switcher 3 is constituted by an analog switch which switches the laser diode drive current ON and OFF. Sampling is not performed immediately after switching to allow time for the emission output to stabilize. If the stabilization time is too long, the time for one measurement becomes too long to be practical. The switching is arranged so that the laser diodes are operated in alternation, not at the same time. This makes it possible to increase the reliability of the measurement and decrease the amount of irradiation received by the subject.

The light receiver 4 comprises a photodiode (PD) 24 that receives scattered light from the subject 12 via a receiving optical fiber 10, and converts this light into an electrical signal that corresponds to the intensity of the light. A detector 11 is disposed so that the end of the receiving optical fiber 10 is adjacent to the end of the projection optical fiber 9. When the area around the measurement region on the subject 12 is so bright that it hinders measurement, or when stray light is a problem, the surface of photodiode 24 is provided with a filter that only transmits light that is of the same wavelength as the laser. Using the filter makes it possible to carry out measurements in bright places.

The FFT (Fast Fourier Transformation) section 5 uses an A/D converter to digitize time-series data of the signals produced by the light receiver 4 corresponding to the intensity of the received light, thereby establishing the power spectrum. The processor 6, which is constituted by a microprocessor or the like, performs function fitting on the power spectrum to calculate the area of the power spectrum. The calculated area is used as a basis for calculating the oxygen saturation. The output section 7 outputs the result of the oxygen saturation calculation to a display or printer.

The measurement operation using the above arrangement will now be described. Under the control of the processor 6, first the light source switcher 3 applies a drive current to light source 1, which emits a laser beam at a wavelength of around 680 nm. This laser beam passes via the synthesizer 8 and projection optical fiber 9 to the subject 12, and is scattered thereby. The scattered light from the subject 12 passes via the receiving optical fiber 10 and is received by the photodiode 24, where it is converted into an electrical signal that corresponds to the intensity of the light. This electrical signal is input to the FFT section 5 for conversion to a power spectrum, and is then input to the processor 6.

The processor 6 processes the power spectrum, subjecting it to fitting using exponential functions. The integration value of the processed functions are then obtained with respect to frequencies from zero to infinity. The light source switcher 3 is then used to switch OFF light source 1 and switch light source 2 ON. The 805 nm laser beam thus emitted is also projected onto the subject 12 and the light scattered by the subject 12 is received and subjected to power spectrum conversion, fitting, and integration. The integration value ratio obtained at each wavelength is then compared with the level of oxygen saturation in the blood to obtain a working curve, which is used to calculate the blood oxygen saturation level.

Details of the power spectrum processing and calculation of the saturation level will now be described. First, dark noise is subtracted from the obtained power spectrum. The power spectrum from which the dark noise has been removed is then subjected to a low-frequency cutoff of 500 Hz or below in order to eliminate noise caused by vibration of the apparatus or subject. Also, to eliminate the effect of the cutoff frequency of around 20 kHz used in the light receiving and amplification circuits of this embodiment, a high-frequency cutoff of 20 kHz or above is used. The power spectrum from 500 Hz to 20 kHz is then subjected to fitting, using the method of least squares. Based on experiments it was found that it was preferable to use an exponential function as the fitting function. Using an exponential function also facilitates method of least square calculations and handling of equations. If $\omega$ is frequency and F the fitting function, then $$F = Ae^{-\omega/\omega_0}$$

Here, A is the power spectrum value when $\omega=0$, that is, the direct current component. $\omega_0$ is a quantity denoting the slope of the power spectrum, and corresponds to the velocity of the blood flow.

The area of the power spectrum can be thought of as the number of scattering bodies, that is, as a quantity corresponding to the number of red blood corpuscles, and not dependent on blood flow velocity. The integration value of the fitting function is used to find the area of the power spectrum. Compared to finding the area by direct means, using the fitting function makes it possible to reduce the effect of noise. Also, integrating the fitting function from zero to infinity makes it possible to incorporate effects from each end of the fitting range, i.e., from low frequencies below 500 Hz and high frequencies above 20 kHz. With this method, the area of the power spectrum can be evaluated with better precision. If S is the area of the power spectrum, then $$S = \int_0^\infty F d\omega$$
$$= \int_0^\infty A \cdot e^{-\omega/\omega_0} d\omega$$
$$= -A\omega_0$$

Values S1 and S2 are obtained for the two wavelengths. There is a correlation between the ratio S1/S2 and the degree of oxygen saturation, so the value can be used to non-invasively measure the oxygen saturation of the subject's blood.

Figure 2:
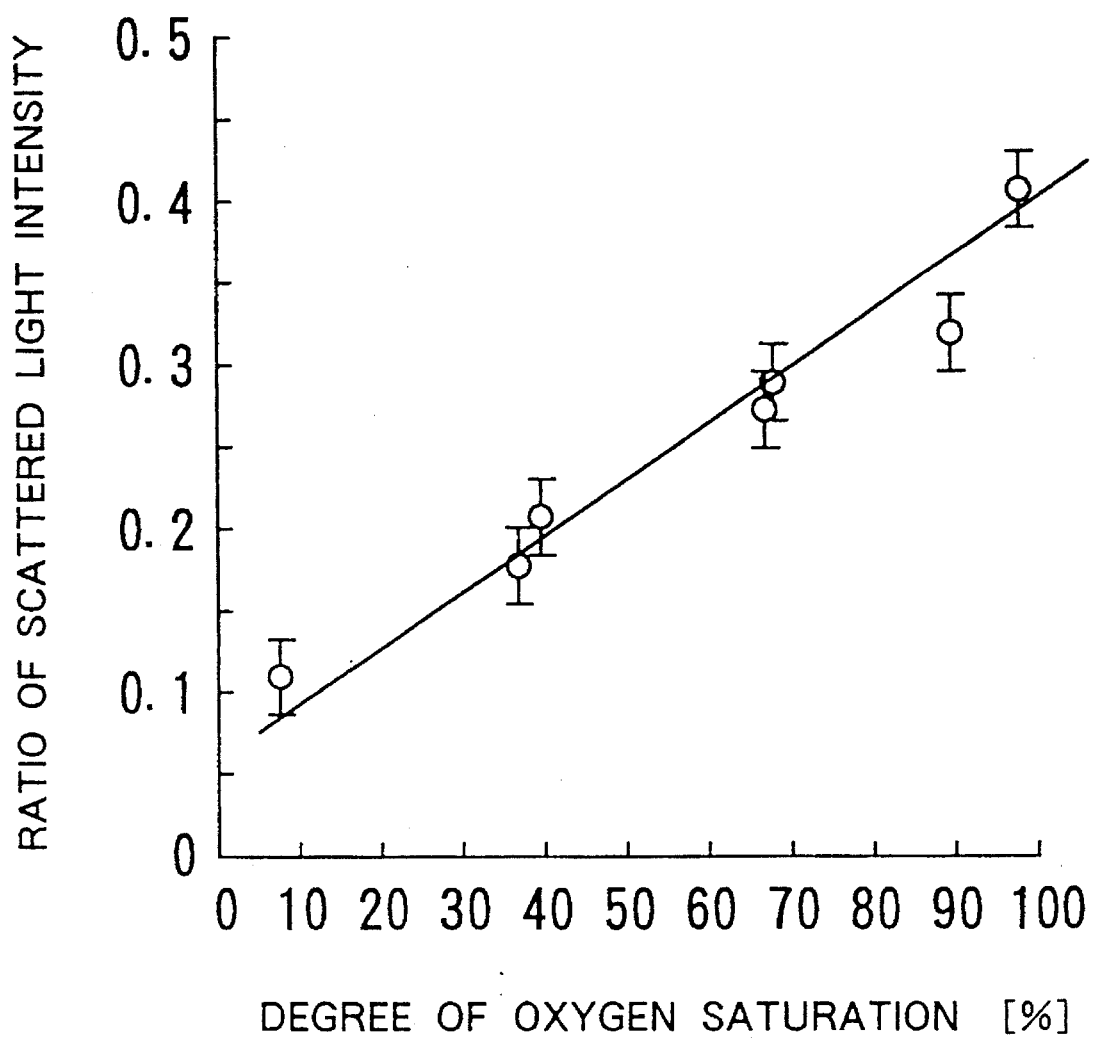
FIG. 2 is a graph showing the correlation between oxygen saturation and scattered light intensity ratio, obtained from measurements made using a living body model.

FIG. 2 shows the relationship between oxygen saturation and scattered light intensity ratio, obtained with the apparatus using a living body model. TEFLON (polytetrafluoroethylene) blocks were used as the tissue model, silicon tubing was used to form the blood vessels, the blood was preserved horse blood, and a peristaltic pump was used to produce a blood flow. The horse blood was circulated through the silicon tubing set into the TEFLON blocks. For measurement, the oxygen saturation level was varied and compared with the scattered light intensity ratio corresponding to the blood flow obtained at each wavelength. The wavelengths used were 632.8 nm and 810 nm. FIG. 2 shows the correlation between oxygen saturation and the scattered light intensity ratio obtained from the exponential function fitting. It can be seen that there is good correspondence between the scattered light intensity ratio and the level of oxygen saturation. This means that the apparatus arranged according to this embodiment enables the oxygen saturation to be measured with good precision.

Thus, the above apparatus of this embodiment enables the degree of oxygen saturation to be measured with high accuracy based on the detection of the scattered light intensity, regardless of the presence or absence of a pulsed blood flow. That is, highly accurate measurement of the oxygen saturation is possible both in arterial blood with a very weak pulse and in a blood flow with no pulse such as venous blood. Moreover, irradiating the subject by switching between laser beams of two wavelengths means that the subject receives less irradiation than when two laser beams are used at the same time. As such, even if the amount of irradiation at each wavelength is slightly increased, measurement accuracy can be improved without adversely affecting the subject.

Figure 3:
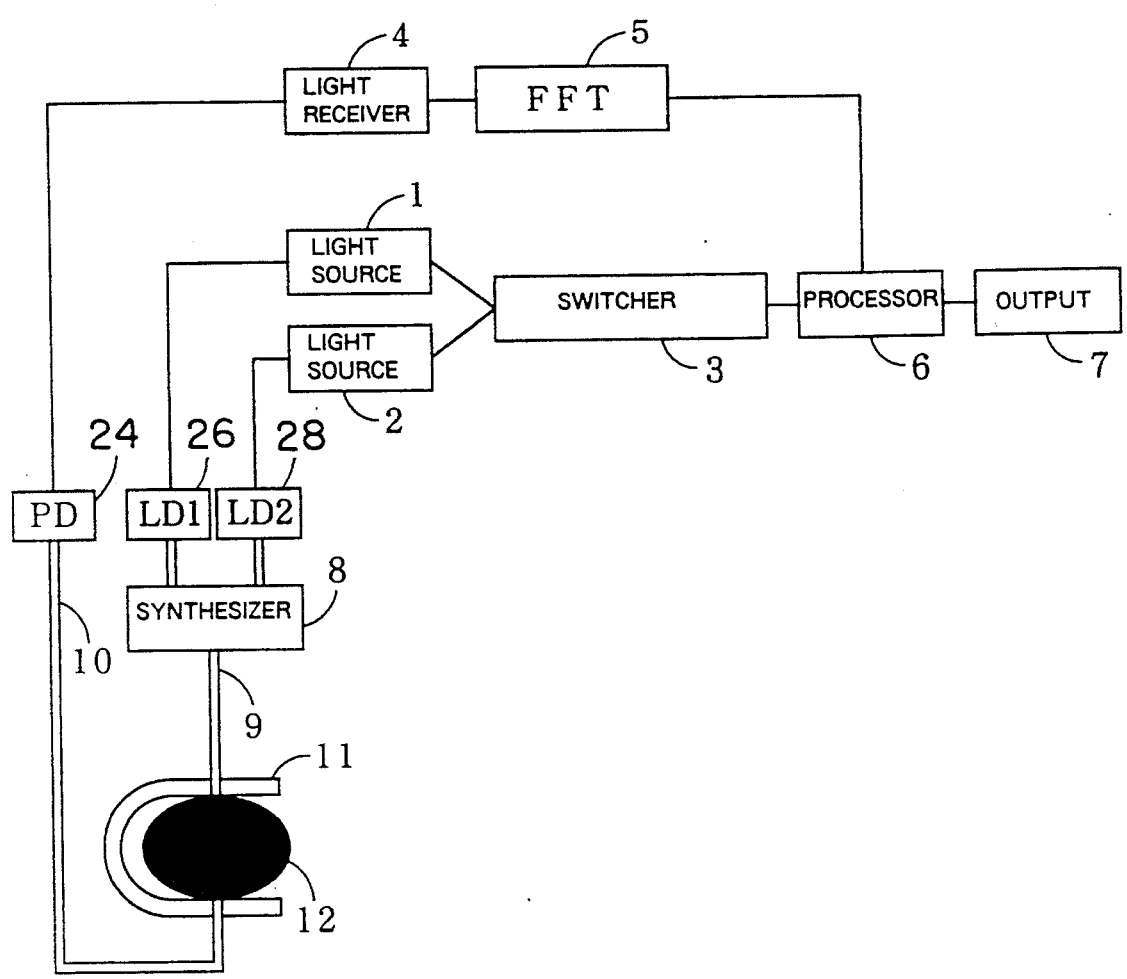
FIG. 3 is a block diagram of a second embodiment of the invention.

FIG. 3 is a block diagram showing the arrangement of a second embodiment of the oxygen saturation measurement of the invention. In this embodiment measurement is based on transmitted light. With a transmission-based arrangement, it is possible to measure the oxygen saturation in all tissues of the subject, and monitor oxygen consumption in tissues. Also, during operations in which major blood vessels and organs are exposed, the detector can be applied to parts prone to damage to monitor the oxygen saturation level directly. The subject 12 is inserted into the detector 11. On the detector 11, the projection optical fiber 9 and receiving optical fiber 10 are disposed so that the ends of the fibers are opposite to each other. A laser beam from light source 1 or light source 2 irradiates the subject 12 via the synthesizer 8 and projection optical fiber 9. Light transmitted by the subject 12 goes via the receiving optical fiber 10 and is received by the photodiode light receiver 24. The arrangement of other parts is the same as the first embodiment.

The measurement operation with the above apparatus of the second embodiment will now be described. As in the first embodiment, under the control of the processor 6 the light source switcher 3 is operated to energize light source 1, producing a laser beam of a first wavelength. The laser beam passes through the synthesizer 8 and the projection optical fiber 9 to irradiate the subject 12. Light transmitted through the subject 12 enters the receiving optical fiber 10 and is received by the photodiode 24, which converts the light to an electrical signal. The electrical signal is converted to a power spectrum by the FFT section 5 and is then input to the processor 6. The processor 6 uses an exponential function to subject the power spectrum to fitting processing.

The light source switcher 3 then switches off light source 1 and switches on light source 2, and the subject 12 is irradiated in the same way, and light transmitted by the subject 12 is converted to an electrical signal, and then to a power spectrum which is subjected to fitting using an exponential function. The subsequent procedure is the same as in the case of the first embodiment, with the ratio of the integration value of the fitting function being obtained with respect to frequencies from zero to infinity, for both wavelengths. The integration value ratio thus obtained is compared with the level of oxygen saturation in the blood to obtain a working curve, from which the blood oxygen saturation level can be calculated. Thus, with the arrangement of this embodiment, the effect provided by the transmission system is obtained together with the effect provided by the first embodiment.

Figure 4:
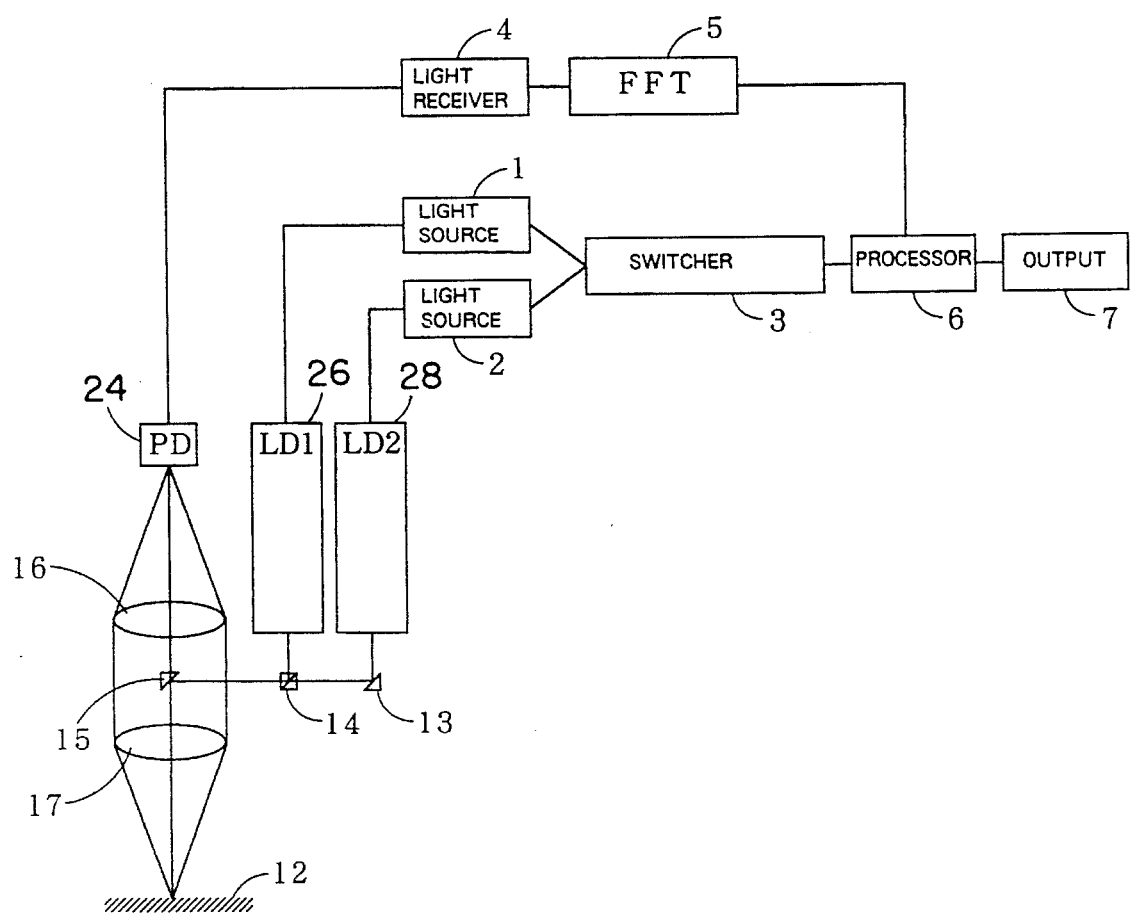
FIG. 4 is a block diagram of a third embodiment.

FIG. 4 shows the arrangement of a third embodiment in which there is no contact between detector and subject. This arrangement is needed when a contact type system cannot be used, such as when the subject is suffering from burns and certain injuries. As in the first two embodiments, this embodiment uses two lasers with different wavelengths. In this embodiment, the receiving optical system and projection optical system both use the same light path for part of the way. This arrangement facilitates the adjustment of the positions of the light receiving surface and laser incident surface. Arranging the system so that the position of the subject surface is optically conjugate with the light receiving surface clarifies the relationship between the subject surface and light receiving surface, enabling the measurement region to be clarified.

In FIG. 4, the laser beam emitted by light source 1 is reflected by a beam splitter 14 and prism 15, and focussed by a lens 17 onto the surface of the subject 12. Scattered light goes via lenses 17 and 16 to the light receiver 4. The laser beam from the light source 2 is reflected by a prism 13, transmitted by the beam splitter 14, is reflected by the prism 15 and focussed onto the surface of the subject 12 by the lens 17. Other parts are the same as in the first two embodiments. The measurement operation is also the same, with light source 1 being used first and the resultant scattered light being processed, followed by the energizing of the light source 2 and the processing of the scattered light produced by that beam frequency, and the results are used to calculate the oxygen saturation level. Thus, this embodiment provides the same effect as the first embodiment, in addition to which it enables the oxygen saturation level to be measured without contacting the subject.

In the embodiments described above, measurement is accomplished by irradiating a subject with two laser beams having different wavelengths. However, it is possible to carry out measurements with an arrangement that uses three or more laser beam wavelengths. In each such case, it is to be understood that the radiation amount would be decreased by sequentially energizing the laser light sources. It is also possible to use a single laser source that is able to emit laser beams at a multiplicity of mutually different wavelengths, inwhich case the subject would be irradiated by sequentially switching the laser wavelengths, and then using the same process described with respect to the above embodiments.

As described in the foregoing, in accordance with this invention, there is provided an apparatus for non-invasively measuring oxygen saturation by projecting coherent light, such as laser beams, at a subject and measuring the intensity of the resultant scattered light or transmitted light containing frequency components corresponding to blood flow, and using the measurement results to obtain the oxygen saturation of hemoglobin in red blood corpuscles. The apparatus comprises a plurality of light sources of which each outputs a light beam having a wavelength that differs from the wavelength of the other beams, switching means for sequentially switching the light sources, means for receiving light scattered or transmitted from the living subject irradiated by laser beams from the plural light sources and converting the intensity of such scattered or reflected light to an electrical signal, and processor means for processing the electrical signal output by the conversion means and calculating the oxygen saturation of the hemoglobin. The apparatus of the invention can readily and accurately measure oxygen saturation whether in arterial blood with a very weak pulse or in a blood flow with no pulse, such as venous blood. Moreover, as irradiation is performed by sequentially switching beams of different wavelengths, the amount of laser beam irradiation to which the subject is exposed can be reduced.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiments disclosed as the best mode contemplated for carrying out the invention, but that the invention will include all embodiments falling within the scope of the appended claims.

What is claimed is:

1. An apparatus for non-invasive measurement of oxygen saturation in a sample of blood in tissue of a subject, the apparatus comprising:

light means for irradiating a sample of blood in tissue of a subject with at least a first laser beam and a second laser beam;

switching means for driving the light means and sequentially switching the irradiation of the sample of blood between the first and second laser beams;

photoelectric detecting means for detecting light transmitted through or reflected from the sample of blood and providing an electrical output signal indicative of an intensity of the detected light; and measuring means for measuring the oxygen saturation of the sample of blood from the electrical output signal of the detecting means, the measuring means comprising converter means for converting the electrical output signal of the detecting means to a power spectrum, and processing means for processing the power spectrum and calculating the oxygen saturation of the sample of blood.

2. An apparatus as claimed in claim 1; wherein the first and second laser beams have different wavelengths.

3. An apparatus as claimed in claim 2; wherein the wavelength of the first laser beam is in the region of 680 nm and the wavelength of the second laser beam is in the region of 805 nm.

4. An apparatus as claimed in claim 1; wherein the converter means converts the electrical output signal to a power spectrum by fast Fourier transformation.

5. An apparatus as claimed in claim 1; further comprising means disposed between the light means and the photoelectric detecting means for reflecting and focusing the first and second laser beams onto the sample of blood.

6. An apparatus as claimed in claim 5; wherein the means for reflecting and focusing comprises a beam splitter and a prism for reflecting the laser beams, and at least one lens for focusing the laser beams onto the sample of blood.

7. An apparatus for non-invasive measurement of oxygen saturation in a sample of blood in tissue of a subject, the apparatus comprising:

light means for irradiating a sample of blood in tissue of a subject with at least a first light beam and a second light beam, the first and second light beams having different wavelengths;

switching means for driving the light means and sequentially switching the irradiation of the sample of blood between the first and second light beams;

photoelectric detecting means for detecting light transmitted through or reflected from the sample of blood and providing an electrical output signal indicative of an intensity of the detected light;

converter means for converting the electrical output signal of the detecting means to a power spectrum; and processing means for processing the power spectrum and calculating the oxygen saturation of the sample of blood.

8. An apparatus as claimed in claim 7; wherein the wavelength of the first light beam is in the region of 680 nm and the wavelength of the second light beam is in the region of 805 nm.

9. An apparatus as claimed in claim 7; wherein the converter means converts the electrical output signal to a power spectrum by fast Fourier transformation.

10. An apparatus as claimed in claim 7; further comprising means disposed between the light means and the photoelectric detecting means for reflecting and focusing the first and second light beams onto the sample of blood.

11. An apparatus as claimed in claim 10; wherein the means for reflecting and focusing comprises a beam splitter and a prism for reflecting the laser beams, and at least one lens for focusing the laser beams onto the sample of blood.

12. A method of non-invasively measuring the oxygen saturation in a sample of blood in tissue of a subject, the method comprising the steps of:

sequentially directing at least a first laser beam and a second laser beam onto a sample of blood in tissue of a subject, the first and second laser beams having different wavelengths;

detecting light transmitted or reflected from the sample of blood and providing an electrical output signal indicative of an intensity of the detected light; and measuring the oxygen saturation of the sample of blood from the electrical output signal by converting the electrical output signal indicative of the intensity of the detected light to a power spectrum, processing the power spectrum, and calculating the oxygen saturation of the sample of blood from the processed power spectrum.

13. A method as claimed in claim 12; wherein the electrical output signal is converted to a power spectrum by fast Fourier transformation.

14. A method as claimed in claim 12; wherein the light transmitted or reflected from the sample of blood is detected by a photoelectric detector.

15. A method of non-invasively measuring the oxygen saturation in the blood of a subject, the method comprising the steps of:

sequentially directing at least a first light beam and a second light beam onto a sample of blood in tissue of a subject, the first and second light beams having different wavelengths;

photodetecting light transmitted or reflected from the sample of blood and providing an electrical output signal indicative of an intensity of the detected light; and converting the electrical output signal indicative of the intensity of the detected light to a power spectrum, processing the power spectrum, and calculating the oxygen saturation of the sample of blood from the processed power spectrum.

16. A method as claimed in claim 15; wherein the electrical output signal is converted to a power spectrum by fast Fourier transformation.

* * * * *